United States Patent [19]

Ferkany

[11] Patent Number: 5,151,184
[45] Date of Patent: Sep. 29, 1992

[54] FLUID COLLECTING AND DISPENSING SYSTEM

[75] Inventor: Michael A. Ferkany, Southfield, Mich.

[73] Assignee: Biomedical Devices Company, Pontiac, Mich.

[21] Appl. No.: 613,335

[22] Filed: Nov. 14, 1990

[51] Int. Cl.$^5$ .................... B01D 17/032; B01D 17/12
[52] U.S. Cl. .................................... 210/514; 210/143; 210/258; 210/259; 210/515; 422/99; 422/100
[58] Field of Search .................. 422/99, 100; 210/513, 210/514, 516, 515, 85, 86, 94, 104, 142, 143, 258, 259

[56] References Cited

U.S. PATENT DOCUMENTS

| | | | |
|---|---|---|---|
| 3,401,876 | 9/1968 | Lucas . | |
| 3,565,582 | 2/1971 | Young . | |
| 4,169,060 | 9/1979 | Columbus | 210/516 |
| 4,358,425 | 11/1982 | Finney et al. | 422/102 |
| 4,449,964 | 5/1984 | Westberg et al. | 494/16 |
| 4,615,866 | 10/1986 | Hyde et al. | 422/106 |
| 4,698,311 | 10/1987 | Hall et al. | 436/10 |
| 4,708,940 | 11/1987 | Yoshida et al. | 436/45 |
| 4,847,205 | 7/1989 | Burtis et al. | 436/45 |
| 4,861,553 | 8/1989 | Mawhirt et al. | 422/100 |
| 4,925,627 | 5/1990 | Johnson | 422/99 |
| 4,927,545 | 5/1990 | Roginski | 210/745 |
| 5,055,271 | 10/1991 | Golias et al. | 422/100 |

FOREIGN PATENT DOCUMENTS 64-47955  2/1989  Japan .................. 422/100

Primary Examiner—Robert A. Dawson
Assistant Examiner—Sun Uk Kim
Attorney, Agent, or Firm—Andrus, Sceales, Starke & Sawall

[57] ABSTRACT

An apparatus and method for automatically aliquotting liquids, such as blood serum, is described. The invention provides a completely automatic, clean, self-contained system for collecting and aliquotting liquids and simultaneously cleaning the aliquotting system. The system includes a serum loading station, a sensing station, an indexing table for advancing test tubes to a collection station, an aliquotting station and a wash station.

4 Claims, 8 Drawing Sheets

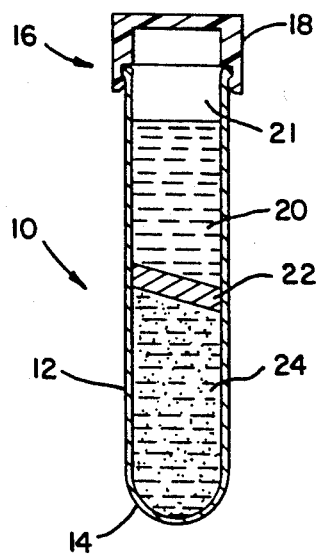
FIG. 1
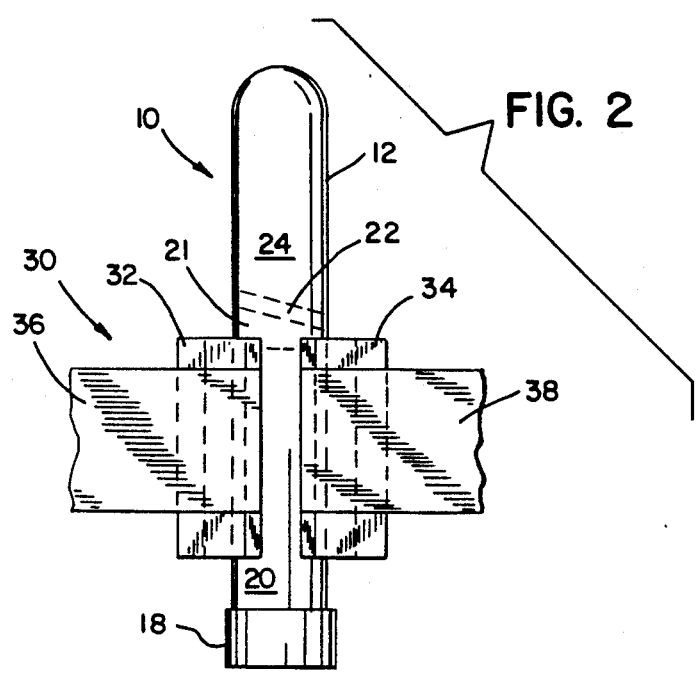
FIG. 2
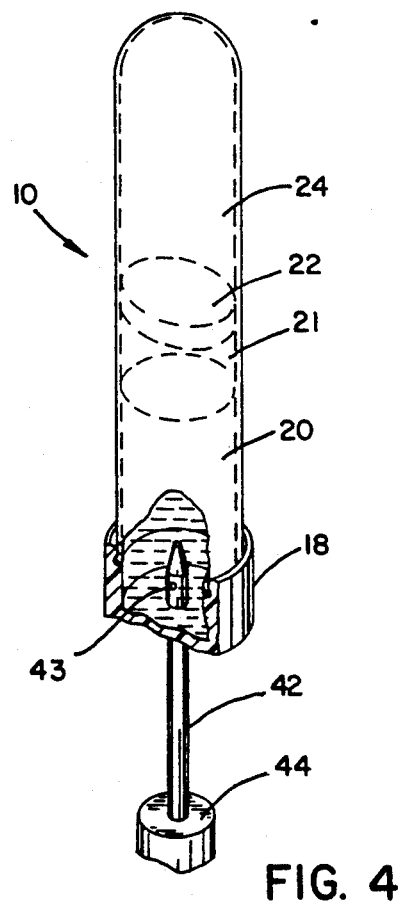
FIG. 4
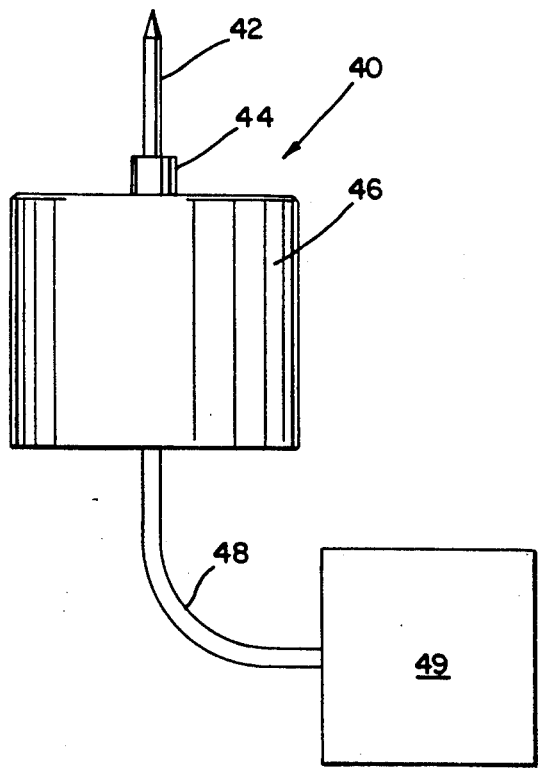

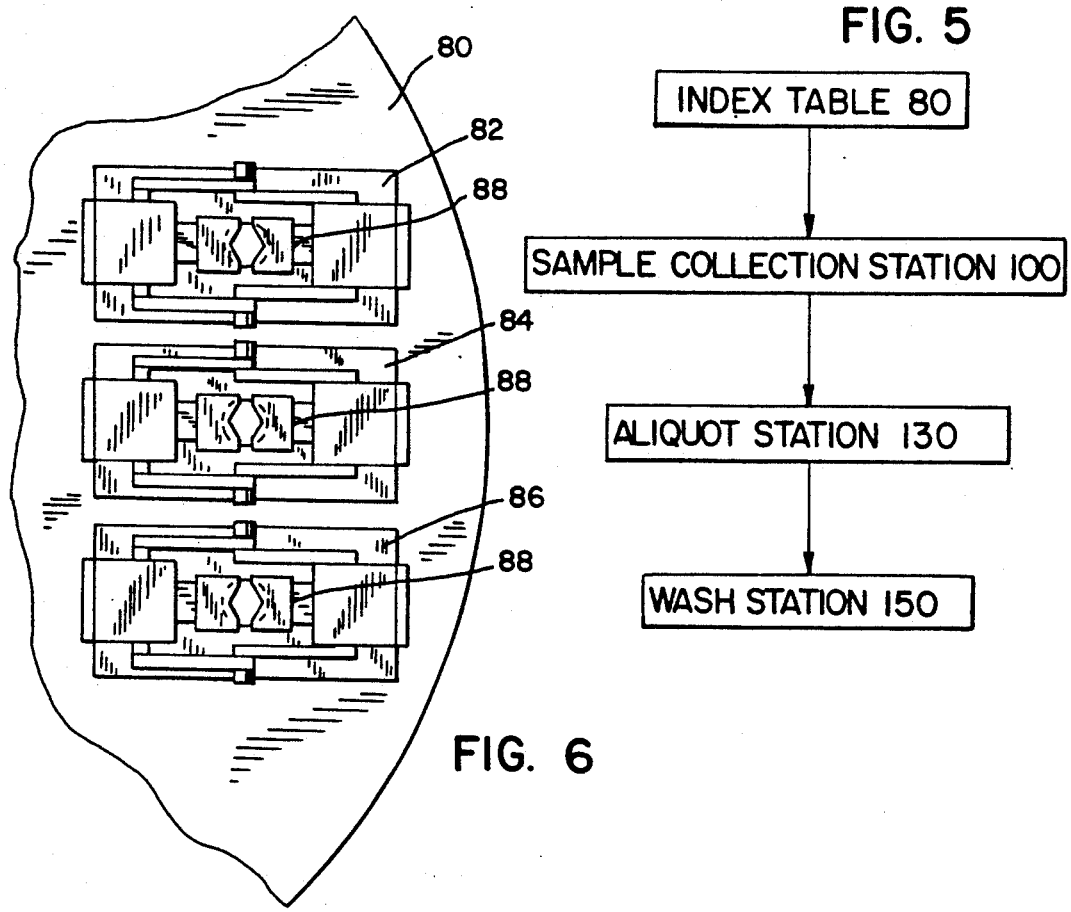
FIG. 5
FIG. 6
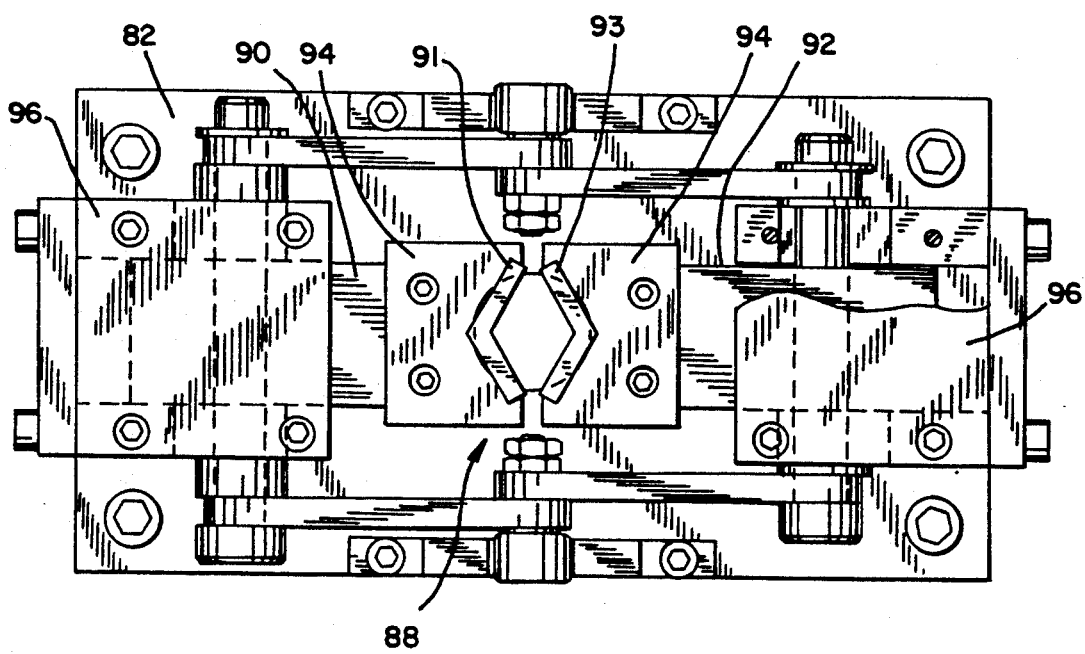
FIG. 7

FLUID COLLECTING AND DISPENSING SYSTEM

BACKGROUND OF THE INVENTION

1. Field of the Invention

The present invention relates to an apparatus, system and method for withdrawing a fluid from a test tube, and more particularly to a system for withdrawing and dispensing a biological fluid such as blood serum. The present invention is more specifically directed to a method and apparatus for continuously and automatically aliquotting a fluid, such as blood serum.

2. Description of the Prior Art

Processes for manipulating sample fluids, generally body fluids such as blood or urine, are conducted on a large scale in laboratories and hospitals. In the prior art process of collecting blood serum for example, blood is generally drawn into a vacuum test tube and centrifuged to separate the blood components from serum. This process is usually conducted by a technician, who draws blood into a vacuum test tube. The vacuum test tube generally contains a separating gel to separate the fluid contents into three layers: a top layer containing the serum, a middle layer containing the separating gel, and a bottom layer containing plasma. For purposes of the present invention, the term "plasma" is used to identify the whole blood components as opposed to serum. An example of a whole blood components are the red blood cells. The test tube must be centrifuged to separate plasma from serum.

After the test tube has been centrifuged, it is examined to determine whether the components have sufficiently separated to be accepted for further testing. If the sample fluid is acceptable, the serum is removed from the test tube in one of two ways: 1) the cap is removed from the tube and the serum is hand-poured into another receptacle; or 2) a needle is inserted through the cap in the top serum layer such that the end of the needle is at a position adjacent, but not touching, the middle separating gel layer. It is extremely important not to touch the needle to the middle layer to avoid plugging up the needle.

The disadvantage of the first method of removing serum, i.e., hand-pouring, is that it is extremely inefficient, requiring a substantial amount of the technician's time to perform the necessary operations, possible excess withdrawal, and there is a possibility of contact with the blood thereby contaminating the blood for further testing and possibly contaminating the technician with diseases carried in the blood. In the second system, the disadvantage is that the extraction needle may inadvertently draw up plasma, or accidentally enter the separating gel barrier in an attempt to get the last of the serum thereby plugging the needle.

The following is a list of prior art references which discuss varying embodiments of liquid separation and inspection techniques.

U.S. Pat. No. 4,449,964 to Westberg et al. is directed to a decanting centrifuge for processing liquid materials. The tubes holding the liquid to be decanted are centrifuged about an axis as defined by the rotor. The amount of liquid to be decanted is controlled by the position of the rotor as it controls the amount of liquid to remain in the tube.

U.S. Pat. No. 3,401,876 to Lucas is directed to a similar type centrifuge as Westberg et al. with an additional axis of rotation. In this invention, the sampling tubes remain upright and the liquid material is decanted during centrifugation due to gravitational forces. This causes the lighter liquids to rise up and out of the tube.

U.S. Pat. No. 4,708,940 to Yoshida et al. is directed to an apparatus for analyzing body fluids such as blood. The apparatus includes a sampling section, i.e., a centrifuge, and an analyzing section. The liquid to be tested, which has been placed in a series of tubes, is positioned in the centrifuge for separation. After separation, a withdrawing pipe is lowered to the tubes and plunged into the separated liquid components. A liquid level sensing electrode detects the depth of plunge and halts the lowering operation at a set level. The liquid is then withdrawn and pipe-pumped to the analyzer. Various measurements of the components of the liquid are then calculated by a data processing unit and the result of the analysis is displayed on a CRT display and recorded on a printer.

U.S. Pat. No. 4,358,425 to Finney et al. is directed to a tube for use in a centrifuge having a penetrable end by needle for drawing a sample of centrifuged liquid.

U.S. Pat. No. 4,847,205 to Burtis et al., U.S. Pat. No. 3,565,582 to Young and U.S. Pat. No. 4,698,311 to Hall et al. are directed to centrifuges in general and their medical applications.

U.S. Pat. No. 4,169,060 to Columbus is directed to a tube for collecting and separating a two-phase liquid, such as blood. The tube includes a partition, which can be used to separate serum from plasma, thus allowing serum to be easily removed by pouring. The partition can be an inorganic thixotropic polymeric gel, which is inert to blood serum.

U.S. Pat. No. 4,615,866 to Hyde et al. is directed to a fluid sampling and analyzing system, in which quantities of serum are withdrawn from a specimen container for analysis. The serum is withdrawn from an upright container by a tube attached to a pump.

U.S. Pat. No. 4,927,545 to Rocinski is directed to an apparatus for automatically sampling and analyzing blood serum. The apparatus includes a centrifuge, an optical sensing unit for receiving information from the centrifuged test tubes, an aspirator needle, which is designed to be placed in an upright test tube for withdrawing fluid, and a computer designed to analyze the output signals of the optical sensing unit.

SUMMARY OF THE INVENTION

The present invention is directed toward a method and apparatus of withdrawing a liquid such as blood or urine from a test tube, wherein the test tube has a closed end and a stopper-sealed or capped end. The method includes positioning the test tube in a substantially vertical manner such that the capped end is located at the bottom of the test tube. A tubular needle is then inserted through the bottom of the test tube, i.e., through the self-sealing cap, such that the needle penetrates the cap only far enough to expose the orifice of the needle. A vacuum is then applied to the needle to draw the liquid through the needle and out of the test tube.

This invention can be expanded to include the steps of identifying accepted or rejected test tubes by determining the quantity of liquid in the test tube in order to establish whether there is a sufficient quantity of liquid to classify the test tube as an accepted test tube. The liquid is aliquotted after it has been withdrawn by dispensing measured amounts of the liquid into aliquot tubes. A preferred method of determining the quantity of liquid in the test tube is a three-step procedure including 1) identifying the length and width of the test tube, 2) determining the level of liquid in the test tube, and 3) analyzing this information to determine the quantity of liquid in the test tube.

The present invention is further directed to a method of continuously and automatically processing test tubes containing a liquid to be aliquotted, wherein the test tube has a closed end and an open end which has been closed off by a self-sealing cap. The method includes inverting the test tubes and positioning them in a substantially vertical manner such that the capped end is located at the bottom of the test tubes, identifying the accepted or rejected test tubes according to the manner described previously, positioning each of the accepted test tubes over a tubular extraction needle, inserting the needle through the self-sealing cap located at the bottom of the test tube such that the needle orifice barely penetrates the cap, drawing the liquid through the needle and out of the test tube into a liquid holding chamber, and dispensing measured amounts of the liquid from the liquid holding chamber through the needle and into a series of aliquot tubes. The liquid holding chamber and needle from which liquid has been dispensed is positioned at a wash station. The previously used liquid holding chamber and needle is simultaneously washed while a second liquid holding chamber continues the withdrawing and dispensing steps. After the liquid holding chamber and needle have been washed, they are positioned in line to further draw liquid from accepted test tubes for aliquotting.

The preferred apparatus of the present invention is a self-contained and automatic aliquotting system, which has the following stations: 1) loading station; 2) sensing station; 3) test tube load assembly station; 4) sample collection station; 5) aliquotting station; and 6) wash station.

One advantage of the present invention is that it is a completely closed system in that no atmospheric atomization of the blood will occur. Further, it is more efficient and faster than the prior art system. Additionally, it is a completely automatic system, thereby obviating the requirement for humans to handle the fluids. This is especially important when the liquid is a body fluid such as blood, blood serum or urine. Such fluids may carry diseases harmful to the operating technician. Another important advantage of the present invention is that the wash operation, in which the sample collection devices are washed, can proceed at the same time the liquid is being collected, thus saving time and assuring adequate time to wash. In the prior art, the system had to pause processing for a sufficient amount of time, i.e., approximately 30 seconds to one minute, in order to clean these devices. This delay extended the time required for handling the serum operation.

Further objects, features and advantages of the invention will be apparent from the following detailed description when taken in conjunction with the accompanying drawings.

BRIEF DESCRIPTION OF THE DRAWINGS

In the drawings:

FIG. 1 is a cross-sectional view of a test tube utilized in the present invention, containing a centrifuged blood specimen.

FIG. 2 is a partial perspective view of the sample collection device of the present invention.

FIG. 4 is a perspective, partial cross-sectional view of an inverted test tube with the needle of a sample collection device penetrating therethrough.

FIG. 5 is a flow chart to help explain the automatic sample collection system of the present invention.

FIG. 6 is a top elevated view of one embodiment of an index table of the present invention.

FIG. 7 is a partial cross-sectional, top elevated view of a test tube holding fixture illustrated in FIG. 6.

DETAILED DESCRIPTION OF THE INVENTION

Figure 3:
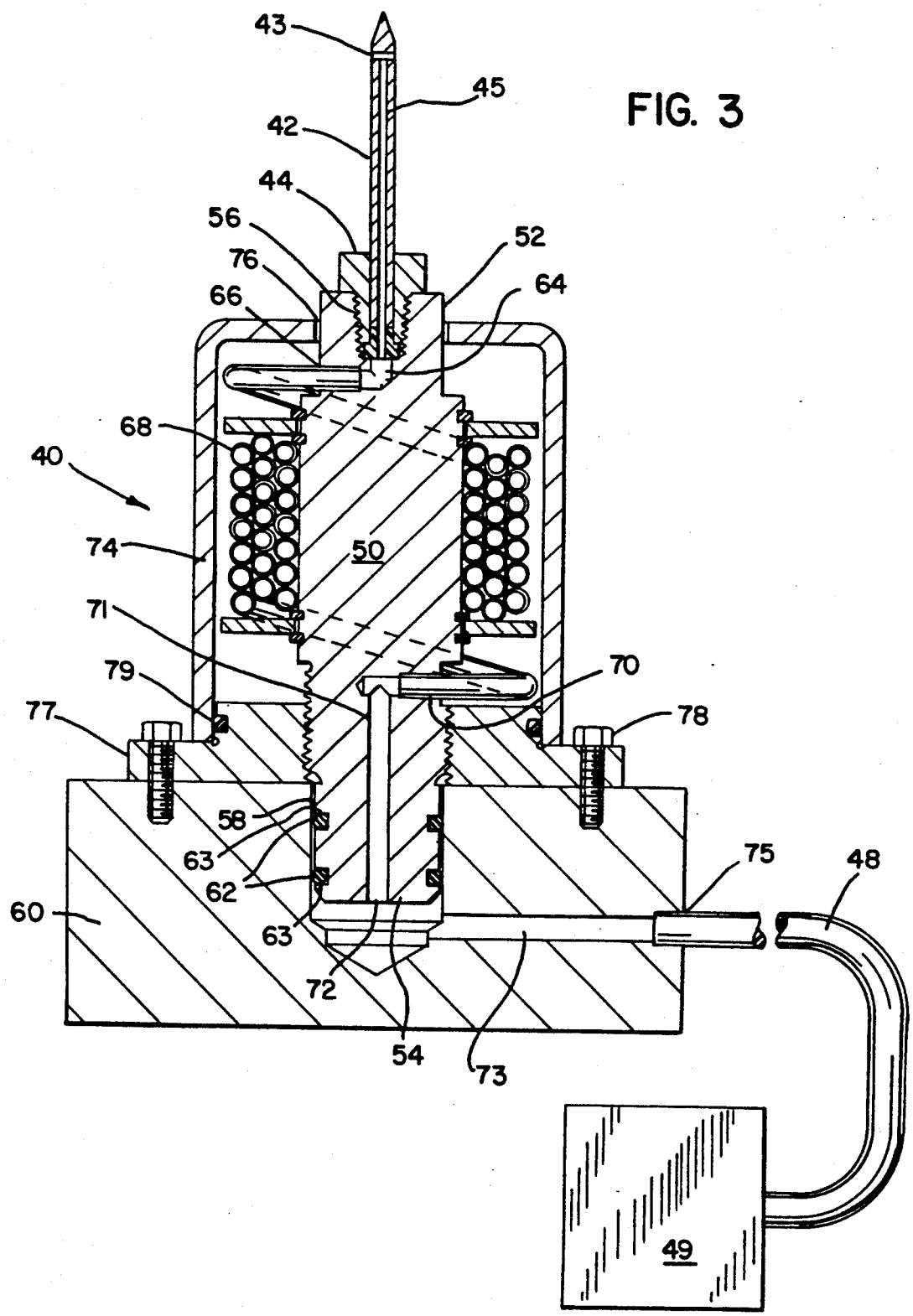
FIG. 3 is a cross-sectional view of a preferred embodiment of a sample collection device of the present invention.

The present invention is generally directed to a system and method of withdrawing a fluid from one or more test tubes and specifically to a completely automatic, clean, self-contained system for collecting and dispensing or aliquotting liquids. While the apparatus of the present invention may be applied to a variety of fluids, and specifically biological fluids such as blood and urine, the present invention will be described with specific reference to blood serum. Unless otherwise indicated, the blood serum will be referred to as "serum" or "sample fluid."

In order to obtain blood serum for testing, the blood serum must first be separated from the plasma. The separation process is most efficiently accomplished in a centrifuge. Centrifuges are well known to the art. Prior to the centrifuge process, samples of whole blood, from which the desired blood serum will be obtained, are placed in test tubes. The blood serum is separated from plasma in the centrifuge by rotating the test tubes at an incline with respect to a vertical axis at a speed sufficient to "spin down" or separate the heavier plasma from the blood serum.

Reference will now be made to the drawings wherein the same or similar features throughout the various figures will be designated by the same reference numbers.

Test Tube

Although there are a variety of acceptable test tubes in the market which will accommodate the separation techniques required to obtain blood serum from whole blood, a preferred example of a test tube is illustrated by the reference number 10 in FIG. 1. The test tube 10 includes a test tube body portion 12 with a generally rounded closed end 14 and a stopper-sealed or capped end 16 which is sealed by a self-sealing cap 18.

The term "self-sealing," as used herein, indicates that the cap 18 may be punctured by a needle, such as a hypodermic syringe needle, in order to withdraw fluid from the test tube. Once the needle has been withdrawn, the cap 18 will automatically self-seal thereby preventing any liquid from escaping the test tube through the cap.

As illustrated in FIG. 1, the test tube 10 contains blood which has been separated by a centrifuge into a top serum layer 20 containing the blood serum, a middle gel layer 22 containing the separating gel, and a bottom plasma layer 24 containing the whole blood component. An air gap 21 is generally located between the cap 18 and serum layer 20. The separator gel has a density half-way between the densities of the serum and plasma. The separator gel must have a viscosity sufficient to prevent the plasma layer 24 from intermingling with the blood serum layer 20 when the test tube 10 is inverted in order to accomplish the goals of the present invention.

Although a number of capped test tubes may be used within the system, the preferred test tube is an integrated serum separator tube, such as the VACUTAINER ® test tube (Becton Dickinson VACUTAINER Systems, Rutherford, N.J.). The VACUTAINER ® test tubes are precapped test tubes which have been evacuated. The separator gel in an unused VACUTAINER ® test tube is initially located in the bottom of the tube. After blood has been drawn into the tube and the tube has been centrifuged, the heavier plasma components will penetrate the gel and settle below the separator gel. Therefore, the separator gel will provide a barrier between the serum and plasma, as illustrated in FIG. 1.

Sample Collection System

The sample collection system of the present invention is designed to process test tubes which contain either all serum or a similar fluid, or a combination of serum, separator gel barrier and plasma.

One aspect of the novelty of the present invention resides in the placement of the test tube in the sample collection system. After the test tubes have been centrifuged to separate the plasma from the serum, the serum tubes are turned upside down (inverted) prior to extracting the serum from the tube. By inverting the test tube, the serum is now located at the lower or bottom of the tube adjacent the cap, and the plasma are located at the top portion of the tube separated by the separator gel plug. Therefore, the needle required to withdraw the serum from the tube needs only to penetrate the cap to expose the needle orifice in order to extract serum. In this manner, serum can be withdrawn from the test tube in a closed system without the necessity of removing the cap and without concerns that the needle may touch the separator gel plug or cell pellet.

Reference is now made to FIG. 2, which illustrates a partial perspective view of a simplified sample fluid collection system of the present invention. Referring now to FIG. 2, the test tube 10 is shown in inverted position such that the cap 18 is located at the bottom of the test tube body 12. In this configuration, the serum layer 20 is located below the gel layer 22, separated by the air gap 21, and the plasma layer 24 is positioned above the gel layer 22.

The test tube 10 is maintained in its inverted position by means of a gripping device 30. The gripping device 30 may be formed of a number of components known to the art. For purposes of the present invention, a representative gripping device includes a first gripping collar 32 and second gripping collar 34, both of which are designed to form a snug fitting around the test tube 10. The collars 32, 34 may be maintained in snug-fit relationship by a variety of retaining mechanisms (not illustrated) acting upon first and second extension arms 36, 38.

Located below the test tube 10 is a fluid sample collection device 40. In its most basic configuration, the sample collection device 40 includes a penetration and fluid-extraction needle 42, a standard tubular needle with an axially aligned conduit, for drawing serum or other sample fluid into the sample collection device. The needle 42 is preferably a stainless steel shaft having an orifice 43 at its distal end and an axially aligned passageway 45 connecting the orifice 43 to sample collection container 46 at the needle's proximal end. The needle 42 is connected by a collar 44 to the sample collection container 46. In its broadest embodiment, the container 46 is a substantially cylindrical, jar-like container, preferably made of a non-absorbing material, which is designed to receive the fluid sample from the test tube 10.

Attached to the container 46, via a connection tube 48, is a pump 49. The purpose of the pump 49 is to create a vacuum condition on the container 46 when the container 46 is attached to the test tube 10 by way of the needle 42 in order to withdraw the serum from the test tube 10 to the container 46. The pump 49 may be any type of pump known to the art for the purpose of creating a vacuum for use in devices such as that described herein.

Preferred Embodiment of Sample Collection Device

Reference is now made to FIG. 3 for a cross-sectional view of a preferred embodiment of a sample collection device 40 of the present invention. The sample collection device 40 of FIG. 3 includes a solid, substantially cylindrical and centrally located spool 50 having an upper end 52 and a lower end 54. The spool 50 is preferably made of a hard, non-absorbing material such as teflon. The spool 50 includes a passageway 56 drilled or otherwise placed at the upper end 52 to accept the collar 44 of the needle 42. The collar 44 is preferably a plastic, teflon or stainless steel fitting that matches the passageway 56 in the spool 50. The lower end 54 of the spool 50 is designed to fit into an opening 58 of a tooling bar 60 in a snug-fit manner. One or more elastomeric O-ring seals 62 or similar devices are positioned in chambers 63 of the spool 50 to seal the sample collection device 40 to the tooling bar 60. The purpose of the tooling bar 60 is to act as a seat for the sample collection device 40. As will be described hereafter, the tooling bar 60 may be associated with a slide mechanism to automatically raise the sample collection device 46 to the test tube 10.

Extending beyond the passageway 56 of the spool 50 is a right angled chamber 64 which exits the spool 50 at an opening 66 in the side of the spool 50. The opening 66 is preferably a non-threaded opening and connected to a spiral array of tubing 68. The tubing 68 begins at the opening 66 and spirals around the spool 50 back and forth in the manner illustrated, like a spool of thread.

In the preferred embodiment, the sample collection device 40 includes approximately 17 feet of tubing having a diameter which results in a total volume of about 9 ml. For most serum-testing purposes, a 9 ml. volume should be sufficient for accommodating the sample fluid from a test tube. Although a variety of compositions may be contemplated for the tubing, teflon is preferred for its non-absorbing, non-sticking quality.

The spiral of tubing 68 ends at a position near the lower end 54 of the spool 50 and enters a opening 70 of lower channel 71. The lower channel 71 provides a continuing passageway through the spool 50 to the exit opening 72 wherein the passageway continues through a channel 73 provided in the tooling bar 60. The channel 73 exits the tooling bar 60 at opening 75. Attached to the opening 75 is a conduit 48, similar to that illustrated in FIG. 2, which in turn is attached to the pump 49.

Although a single jar-like container may be used to receive the sample fluid from a test tube, as illustrated in FIG. 2, tubing as illustrated in FIG. 3 is preferred to ensure that sample fluid—and only sample fluid—is contained in the tubing. Further, the tubing configuration prevents unwanted and unnecessary movement in the liquid as the sample collection device 40 is moved around.

The tubing 68 is further beneficial in a washing cycle, which will be described in detail hereafter. Briefly, after the sample collection device 40 has been used, it is desirable to wash every area contaminated by the sample fluid. By containing the fluid in tubing, wash water can be forced through the tubing ensuring a high velocity of wash water through the tubing to physically flush away anything that might be on the side walls of the tubing. If an open jar-like container were used, as illustrated in FIG. 2, it may be difficult to ensure that the entire container would be washed. As water is forced from a large opening to a small opening, part of the container would not be touched by the washing action.

A pump 49, similar to that illustrated and described with respect to FIG. 2, is used to control the quantity of fluid withdrawn into the sample collector device. A preferred pump is a peristaltic pump.

A protective cover 74 is designed to fit over the sample collection device 46. The cover 74 has an aperture or open end 76 at the upper end of the covering in order to allow the needle 42 and collar 44 to pass through the cover 74. The cover 74 is seated on a cylindrical collar 77 in a sealed manner by an O-ring 79. The cover 74 and collar 77 are also attached to the tooling bar 60 by a connection bolt 78.

In operation, the sample collection device 46 is placed underneath the test tube 10 as illustrated in FIG. 2. The sample collection device 46 may be manually placed thereunder or mechanically positioned by automated devices. The sample collection device 46 is then elevated to the test tube 10 to a position wherein the needle 42 pierces through the cap 18 of the test tube 10 just enough to penetrate the cap 18 as illustrated in FIG. 4. In this manner the maximum amount of fluid can be obtained with the least amount of needle contact because the cap 18 has been barely penetrated. This method of collection is particularly advantageous in the case of blood serum collection as it avoids any contact between sample collection device 40, via the needle 42, and the gel barrier 22 in the test tube as the gel barrier 22 is sufficiently remote from the cap 18. Thus, substantially all of the fluid can be removed from the test tube 10 without the needle 42 coming close to the gel barrier 22. A peristaltic pump then forces the liquid to be withdrawn from the test tube.

The tubing 68 will be preferably filled with a pump fluid, preferably deionized water, when it is coupled to the peristaltic pump 49. Therefore the pump fluid, along with the collected sample fluid, will be pumped through the tubing. Immediately prior to withdrawing a sample fluid from the test tube 10, the column of pump fluid is slightly withdrawn leaving an air bubble gap having a volume of about one milliliter. Therefore, in essence, pump fluid is positioned throughout the coiled tubing 68 out to the needle 42. When the cap 18 of the test tube 10 is pierced and the sample fluid is withdrawn, a separating air bubble remains between the pump fluid and the sample fluid.

After the sample fluid has been withdrawn from the test tube 10 into the sample collection device 40, the sample collection device 40 is withdrawn from the test tube 10 by lowering the sample collection device 46 such that the needle 42 is removed from the cap 18 of the test tube 10. The sample collection device 40 is now ready to have the sample fluid dispensed or removed.

In the dispensing operation, the pump action is reversed and the pump fluid is forced through the tubing in the opposite direction thus forcing the sample fluid in the opposite direction in the tubing and out of the needle 42. Although the separating air bubble in the tube may become slightly compressed, contact between the sample fluid and the pump fluid will still be substantially avoided.

It will be understood after a review of the entire disclosure that the sample fluid may be dispensed in measured aliquots according to the desired purpose.

Automated Sample Collection System

In another embodiment of the present invention, the sample collection system can be automated to include a fluid dispensing feature in combination with a sample collection device and a wash station. Reference is now made to FIG. 5 which is a flow chart designed to assist in the explanation of the automated sample collection system of the present invention. Without wishing to limit the scope of the present invention, the automated sample collection system as described herein will include reference to three sample collection devices 40 used simultaneously. It is within the scope of the present invention to incorporate more or fewer sample collection devices within the automated sample collection system of the present invention.

In this embodiment, the sample fluid-filled test tubes are placed onto an index table 80. Without wishing to be limited to a particular description of an index table, an acceptable index table for purposes of the present invention is illustrated in FIG. 6. The index table 80 includes three test tube positioning slots 82, 84, 86. Positioned within each slot 82, 84, 86 are spring-loaded gripper fixtures 88, similar to the gripper 30 illustrated in FIG. 2, for releasibly locking the test tubes 10 in inverted position in the index table 80.

Referring now to FIG. 7, which illustrates in close-up one of the test tube positioning slots 82, the gripper fixture 88 includes first and second arms 90, 92 connected to first and second gripping collars 91, 93 respectively. Each arm 90, 92 has a first end 94, to which is attached a gripping collar, and a body 96 which may be manipulated in order to open or close the gripping end.

Thus, the positioning slots 82, 84, 86 in the index table 80 contain centering fixtures to secure each test tube in gripper-like jaws. The preferred embodiment of jaws are spring-loaded rather than electrically or pneumatically operated. In this manner, the gripper fixtures 88 can operate efficiently without the necessity of hoses or electrical wires. By depressing the second ends 96 of each arm 90,92, the gripper fixtures 88 will opened to receive the inverted test tube 10.

Figure 8:
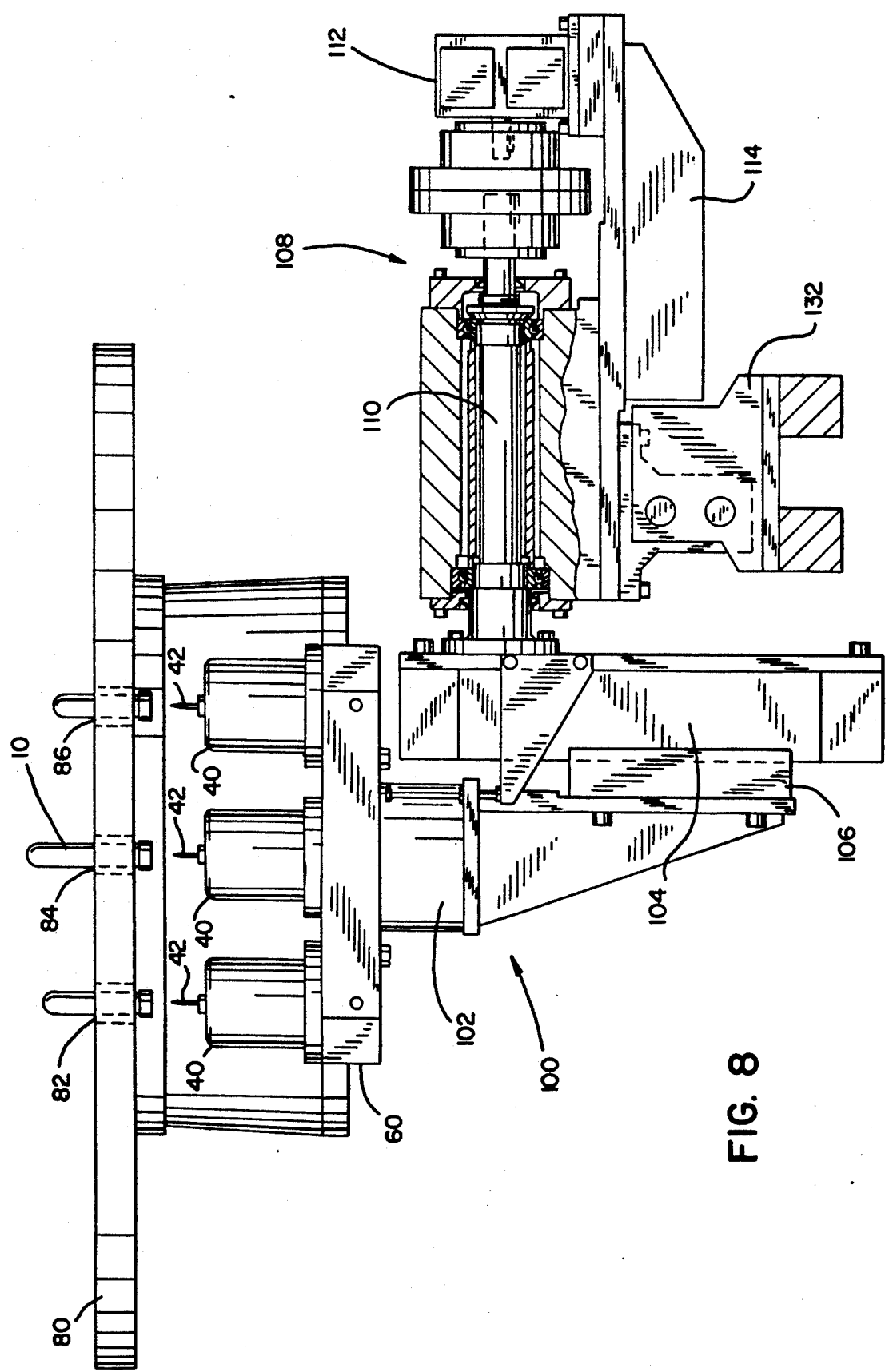
FIG. 8 is a side elevated view of the collection station of the automatic sampling system of the present invention.

Referring now to FIG. 8, there is illustrated a side elevated view of the automatic sample collection station 100 of the present invention. In this embodiment, the automatic sample collection station 100 includes three sample collection devices 40 which are positioned below the index table 80. The purpose of the collection station is to collect a sample fluid from the test tubes 10 which are positioned in the test tube positioning slots 82,84,86 in the index table 80.

The collection station includes the tooling bar 60, first illustrated in FIG. 3, which is designed to hold the sample collection devices 40. For purposes of the present invention, the preferred embodiment of the tooling bar 60 is a slotted rectangular bar designed to hold three collection devices 40 in mating relationship at a time.

The tooling bar 60 is releasably attached to the automatic sample collection system by a tool change device 102 as illustrated in FIG. 8. The tool change device 102 is in turn attached to an activating cylinder 104, such as an air cylinder, carrying a vertical slide mechanism 106. The activating cylinder 104 is provided to raise and lower the slide mechanism 106 with the tool change device 102 and tooling bar 60 to and from the index table 80, which contains the test tubes.

When the activating cylinder 104 is activated, the sample collection devices 40 are elevated to the index table 80. Each needle 2 of the sample collection devices 40 will then pass through the slots 82,84,86 in the index table 80 and pierce the cap 18 of the test tube 10 as illustrated in FIG. 4. As previously mentioned, the needle 42 only has to pass through the cap 18 a sufficient distance such that the end of the needle enters the serum reservoir 20. Thus, there is no possibility of tainting the end of the needle or the sample fluid with the separator gel barrier 22.

A vacuum or suction force is then applied to the sample collection devices 40, via pump 49 (not illustrated in FIG. 8) causing the sample fluid to be withdrawn from the test tube 10 through the needle 42 and into the tubing 68 in the sample collection device 40. After the required amount of sample fluid has been completely withdrawn from the test tubes, the activating cylinder 104 reactivates to retract the sample collection devices 40 to their original positions. The sample collection devices 40 are now ready for the dispensing mode.

In FIG. 8, there is also illustrated a rotary actuator device 108, which is designed to rotate the tooling bar 60, containing the fluid sample filled collection devices 40, approximately 180° so that the needles 42 of the sample collection devices 40 are now pointing downward. The sample collection devices are now ready to aliquot the sample fluid into aliquot tubes.

The rotary actuator 10B includes rotatable spindle 110 fixedly attached at one end to the tooling bar 60, via the vertical slide mechanism 106, and rotatably attached at the other end to a motor 112 which is designed to rotate the spindle 110 and, in turn, the tooling bar 60.

The rotary actuator 108 is positioned in the system on a horizontally moveable platform 114.

Figure 9:
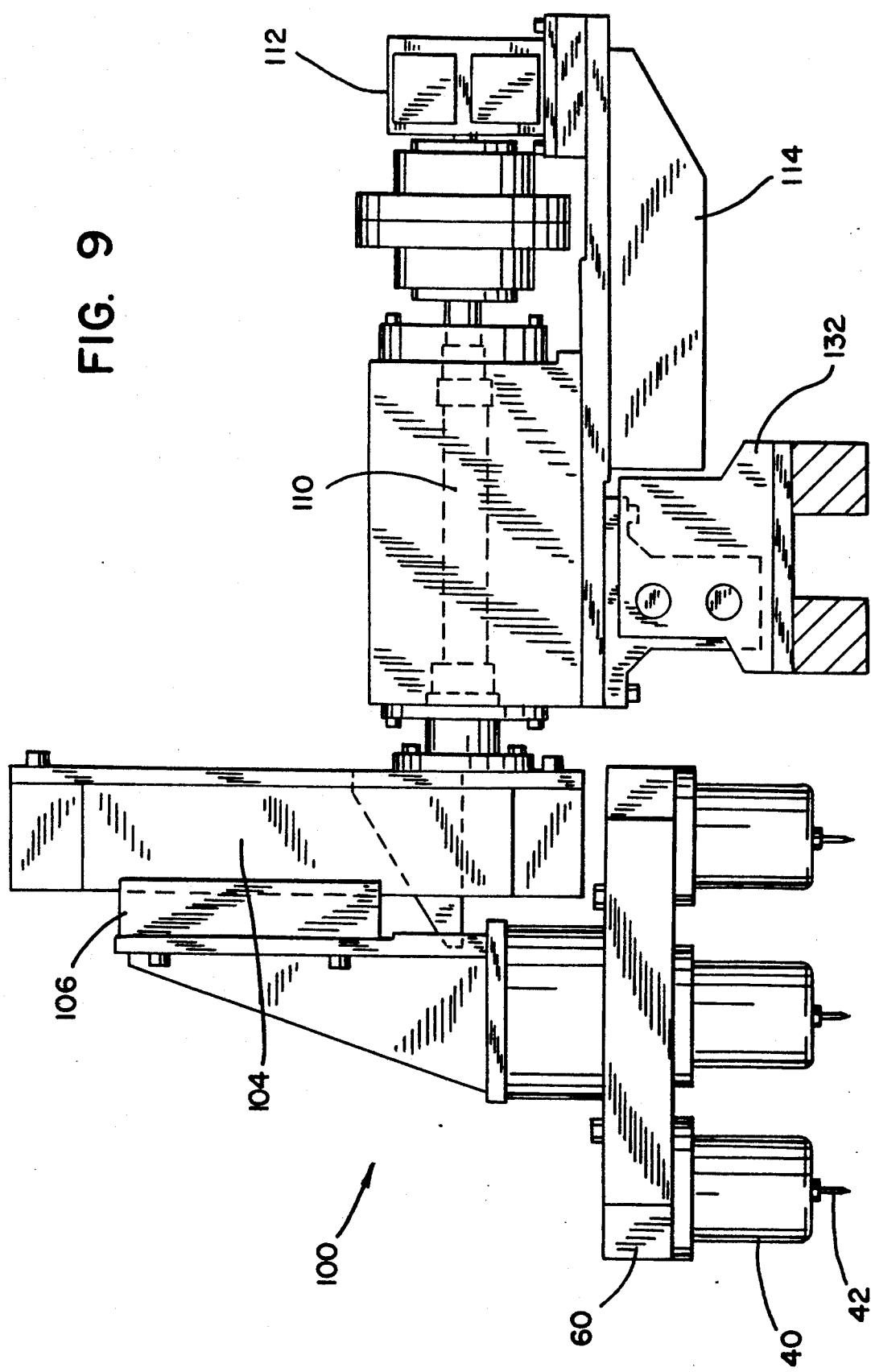
FIG. 9 is a side elevated view of the collection station of the automatic sampling system of the present invention, illustrated in FIG. 8, wherein the sample collection devices have been rotated approximately 180°.

In order to dispense the fluid, the motor 112 must be activated, thereby activating the rotary actuator 108 to rotate the sample collection devices 40 in their 180° journey such that the needles 42 of the sample collection devices 40 are now pointing downward as illustrated in FIG. 9.

After rotation is complete and the needles 42 of the sample collection devices 40 are pointing downwardly, the sample collection devices 40 may then be moved to a dispensing or aliquotting station 130 via a horizontal slide mechanism 132. As will be described hereafter, the aliquotting station may consist of one or more aliquotting tubes designed to receive the sample fluid from the collection devices 40. It is to be noted that the entire sample collection station 100, including the sample collection devices 40, the activating cylinder 104, and the platform 114, containing the rotary actuator 108, is moved horizontally with respect to the slide 132.

The sample collection system of the present invention can also be expanded to include a wash station 150. When the sample fluid in the sample collection device has been dispensed, preferably a small fraction of the sample fluid will remain in the sample collection device 40. The sample collection device is then positioned for the wash cycle.

Unlike standard wash cycles, in which a pump or similar object may be used where the wash liquid is drawn into the sample collection device and pumped out through the same opening, the present invention incorporates a wash cycle in which the wash liquid enters the sample collection device 40 at one end and is forced through the sample collection device 40 at the other end. Thus, the wash cycle pumps out the last bit of serum, the air gap, and then water and wash fluid. In essence, serum has only touched the inside of the tubing and has never made anything but two interfaces: the needle to spool body and the body to the tube.

The wash cycle is therefore a straight-forward, straight-lined, non-disruptive flow of wash fluid in the sample collection device. Because water fills the sample collection device 40 and is the moving force behind the withdraw and the dispense phase of the sample collection, this keeps down bubbling and foaming of the sample liquid.

Figure 10:
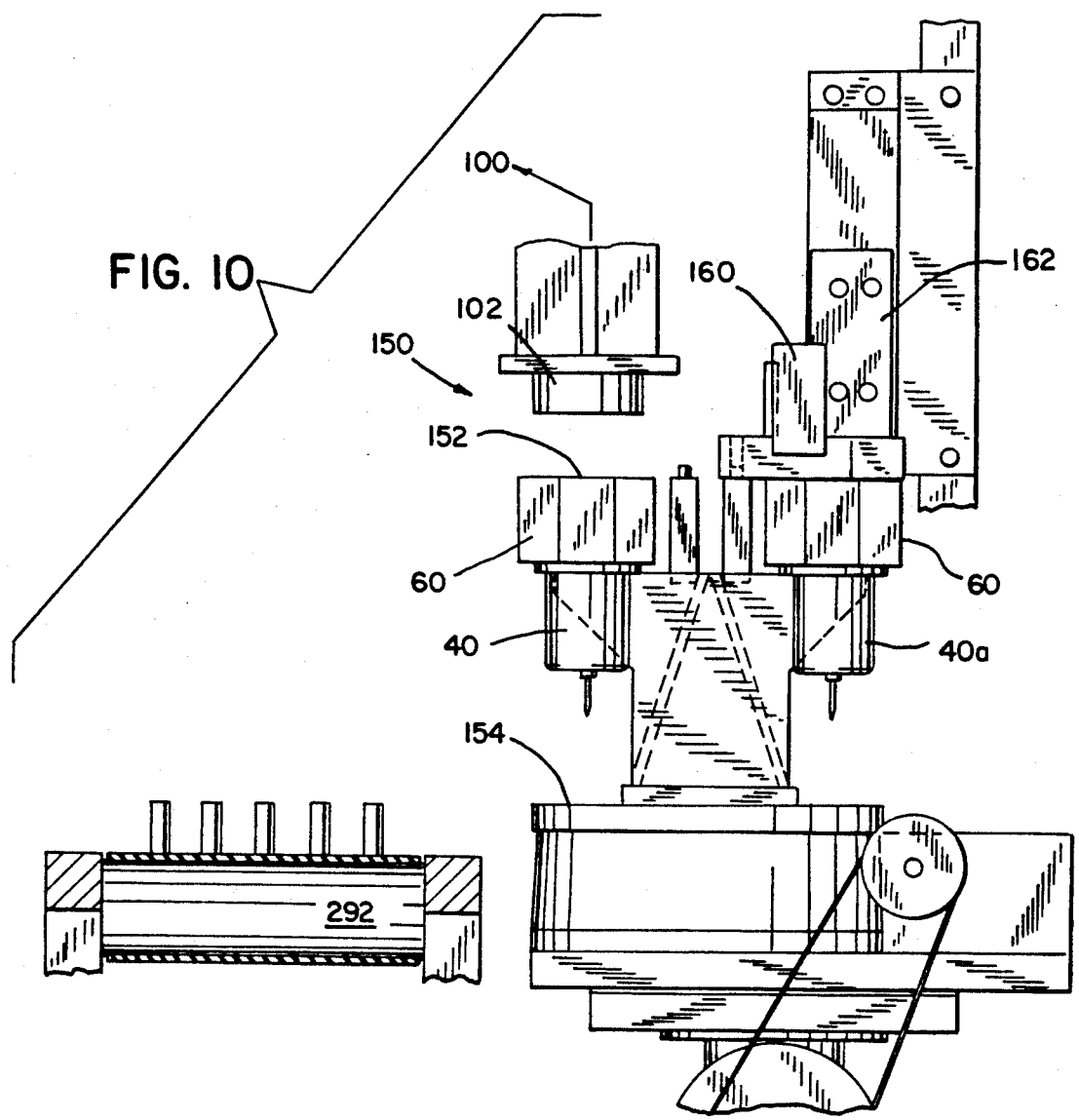
FIG. 10 is a side elevated view of the wash station of the present invention.
Figure 11:
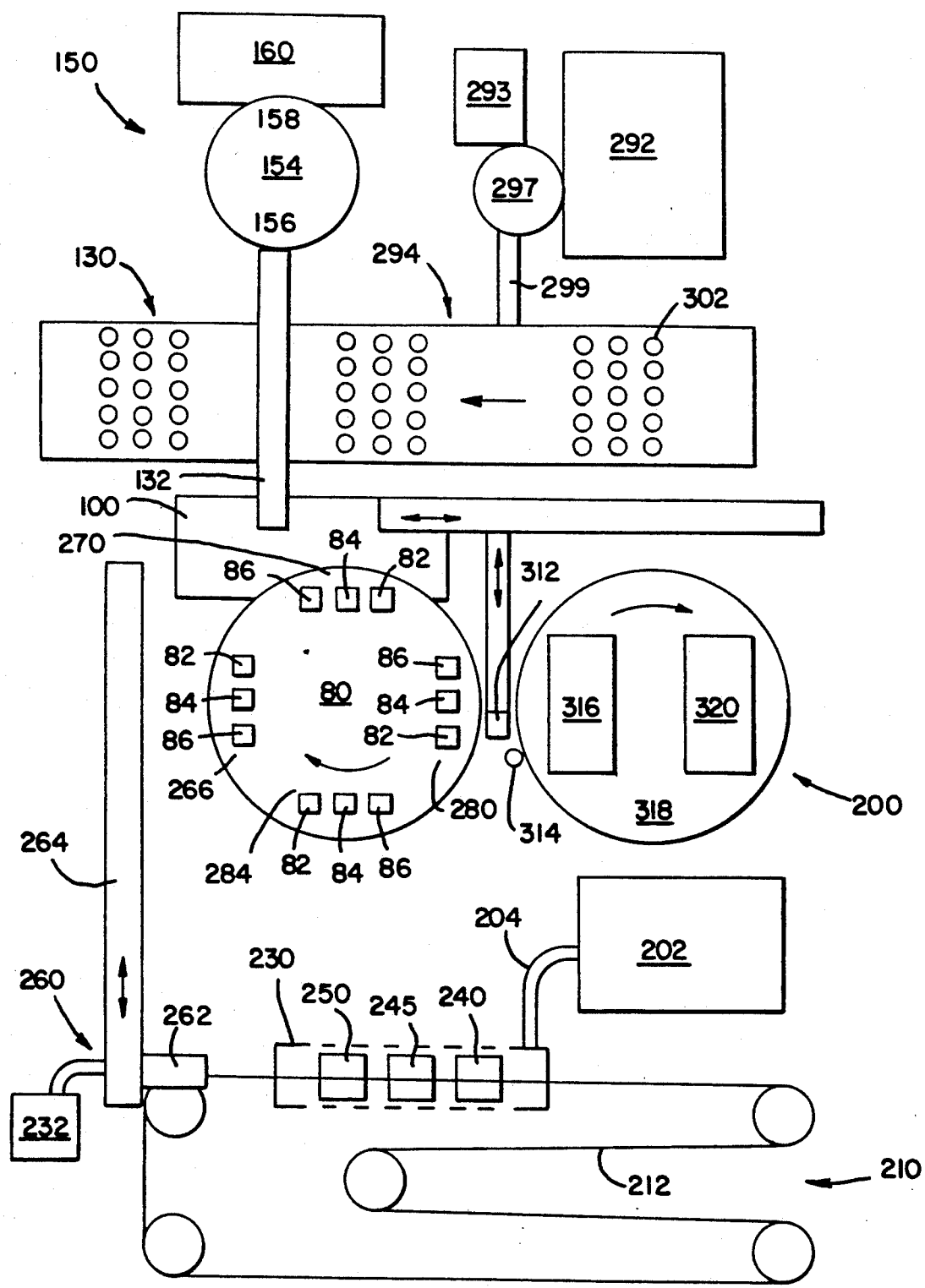
FIG. 11 is a plan view of an automated sample fluid testing system of the present invention.

Referring now to FIGS. 10 and 11, when the fluid has been dispensed from the sample collection device 40, the slide mechanism 132 moves the sample collection device 40 to a wash station 150 and positions the sample collection device 40 over a fixture position 152 on a wash index table 154. The dirty sample collection device 40 is removed and replaced by a clean sample collection device 40a according to the following procedure.

The tool change device 102 is pneumatically coupled to the tooling bar 60 of sample collection device 40. The tool change device 102 is characterized by a robotic tool changer consisting of a tool half and a robot half.

To separate the sample collection device 40 from the sample collection station 100, a computer-controlled signal is generated to pneumatically uncouple the tooling bar 60 from the sample collection station. The whole tooling bar 60 is dropped off onto and nested on tapered pins on the wash index table fixture position 152. Located on the other side of the wash index table 154 is a second sample collection device 40a, which has been cleaned and is ready for fluid sample withdrawal.

The slide mechanism 106 withdraws from the wash station 150, the wash index table 154 rotates thereby positioning the dirty sample collection device 40 from the drop off/pick up position 156 to the wash position 158, and taking the clean device 40a from the wash position 158 to the slide pick-up position. The tool change device 102 is lowered by slide 106 and pneumatically locked onto the cleaned device 40a, slide 106 retracts and returns to the sample collection station for further fluid sample collection.

The wash station 150 includes a cleaning plate 160 mounted on a vertical slide mechanism 162. As described previously, the index table 154 includes two positions: the drop off/pick up position 156 and the wash position 158. The cleaning plate 160 is positioned directly above the wash position 158.

After the dirty sample collection device 40 is lowered to and placed on the wash index table 154 at the drop off/pick up position 156 and is separated from the tool change device 102, the wash index table 154 rotates approximately 180° to place the dirty sample collection device 40 at the wash position 158 and the clean sample collection device 40a at the drop off/pick up position 156. It is to be noted that the sample collection devices 40 and 40a are positioned on the wash index table 154 by protruding pins (not illustrated) to prevent the collection devices from moving about.

Once the dirty sample collection device 40 is placed at the wash position 158, the cleaning plate 160 descends and connects to the tooling bar 60. The connections are made via bushings which connect tubes filled with cleaning fluid from the cleaning plate 160 with the teflon tubing 68 in the collection device 40 via a system of connection bushings (not illustrated).

The cleaning plate 160 is designed to pass solutions throughout the entire tubing structure 68 of the sample collection device 40. Additionally, there is a mechanism designed to clean the outer surface of the needle 42.

The entire cleaning operation is designed to take approximately 30 seconds. While the sample collection device 40 is being cleaned, another sample collection device will be placed at the drop off/pick up position 156 of the wash index table 154. After the sample collection device 40 has been cleaned, the wash index table 154 rotates placing the dirty sample collection device 40 at the wash position 158 and the clean sample collection device 40a at the drop off/pick up position 156 for reuse in the sample collection system.

In this manner the automatic collection device can contain one or more stations, including the sample collection station 100, the aliquotting station 130 and the wash station 150.

Automatic Aliquotting System

Referring now to FIG. 11, there is disclosed a plan view of the preferred embodiment of the present invention illustrating an automated sample fluid testing system 200 according to the present invention.

The sample fluid testing machine 200 herein described is a fully automated machine designed to perform the following functions: 1) receive test tubes containing sample fluid; 2) determine whether the test tubes contain a sufficient amount of sample fluid; 3) accept or reject the test tubes on the basis of the quantity of fluid in the test tube; 4) withdraw the sample fluid from the test tube; 5) aliquot the fluid in measured amounts in previously identified aliquot tubes; 6) remove the empty test tubes and the aliquot tubes; and 7) wash the sample collection and dispensing devices.

The fluid testing system 200 is separated into a series of stations, each having its own function and purpose. The entire system is controlled by a control computer 202 connected to the system by a connection cable 204. The control computer may contain sample handling information or may be connected to a host computer which contains the sample information.

Loading Conveyor

The first station, the test tube loading conveyor station 210, is primarily comprised of an endless conveyor 212. The purpose of the conveyor system 210 is to receive the test tubes for processing by the fluid testing system 200.

Figure 12:
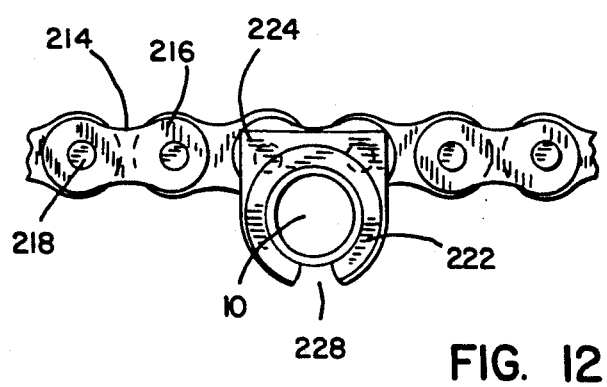
FIG. 12 is a partial top elevated view of the conveyor assembly used in the sample fluid testing system illustrated in FIG. 11.
Figure 13:
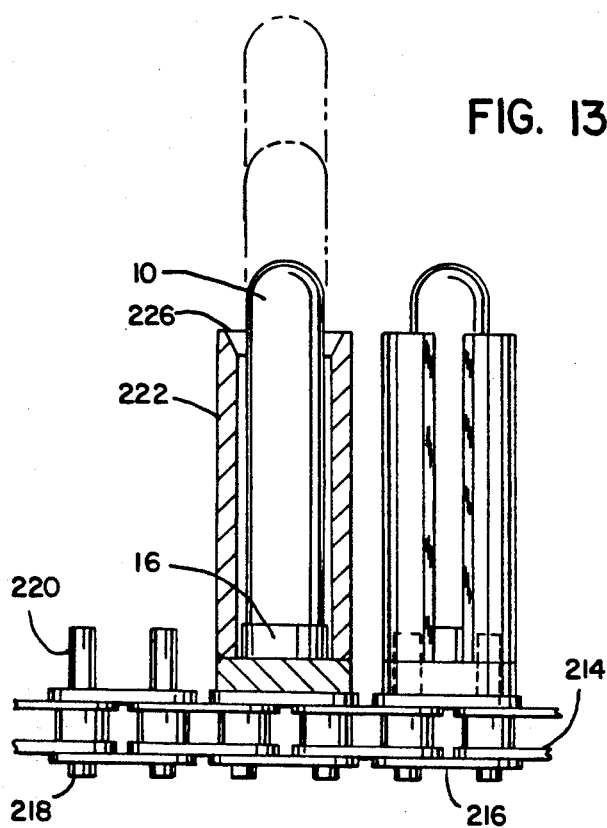
FIG. 13 is a partial side elevated view of the conveyor assembly of FIG. 12.

Reference is now made to FIGS. 12 and 13 for partial top and side elevated views of the conveyor 212. The conveyor 212 includes an endless track 214 of connecting links 216, each of which are rotatably connected by means of a joining post 218. As illustrated in FIG. 13, the post 218 includes an extended member 220. Two contiguous extended members 220 are designed to hold a test tube holder 222.

As illustrated, the test tube holder 222 has a length and diameter sufficient to hold an inverted test tube 10. The diameter of the test tube holder 222 must be sufficient to accommodate the test tube in a loose fitting manner.

The test tube holder 222 may be made of extruded plastic or similar materials, and is characterized by fittings 224 for providing a snap-fit connection to the member 220 of the track 214. The test tube holder 222 is also characterized by an open end 226 to allow test tubes 10 of a variety of lengths to be placed into the holder 222. It will soon be apparent that the opening 226 is necessary in order to manipulate the test tubes 10 for further processing in the system 200. The test tube holders 222 are further characterized by a slot 228 extending the length of the holder 222. The purpose of the slot 228 will become more apparent when the bar code read station is described.

The test tubes 10 are manually loaded onto the conveyor system 32 in inverted position, as illustrated in FIG. 13, such that the cap end 16 is at the bottom of each of the test tube holders 222.

Prior to placing the tubes into the conveyor, a technician will apply an identifying label to the test tube. Generally, the label will be in the form of a code 39 bar code label parallel to the axis of the test tube. The bar code label identifies the specimen relative to information which has been placed into a control computer 202, which will be further explained hereinafter.

The conveyor 212 in the loading station 210 is designed to operate continuously, preferably at a speed of one and one-quarter inches per second. Test tubes are placed in inverted position onto the test tube holders 222 on the conveyor 212. The conveyor 212 will stop for 10 second intervals in order to allow sufficient time to load the test tubes onto the conveyor and pass them onto the next station.

Sensing Station

After the test tubes have been loaded on the conveyor 212, they are transported, via the conveyor 212, to the sensing station 230. The purpose of the sensing station 230 is to determine the amount of serum in the test tubes, compare the determined amount with the required amount, which has been inputted into the control computer 202, and determine whether the tube contains a sufficient amount of serum to be accepted into the aliquotting system.

The sensing station 230 measures the volume of fluid in each tube and compares the measured volume to the total volume required to perform the aliquots requested for the particular specimen. If the measured volume is less than the required volume, the test tube is transported to a reject bin 232 for manual processing. The preferred embodiment of the sensing station 230 includes three substations.

The first substation, the size sense station 240, determines the length and width of the test tube.

The present invention will preferably accept five known sizes of test tubes: 16 mm diameter×85 mm length; 16 mm diameter×100 mm length; 16 mm diameter×12 mm length; 13 mm diameter×100 mm length (hemaguard tube with 16 mm cap); and 13 mm diameter×120 mm length (hemaguard tube with 16 mm cap).

By knowing the length and width of the test tube, the control computer 202 can verify that each test tube received is a proper test tube for the device from previously recorded information in the control computer 202 via a connection cable 204.

In operation, a preferred size sense station 240 includes a series of aligned fiber optic photocell sensing units positioned to activate when a test tube passes by it. The sensor will "read" the height and diameter of the test tube and process the information in the control computer 202.

After the length and diameter of the test tubes are ascertained in the size sense station 240, the test tubes are next conveyed to the bar code read station 244. The purpose of the bar code read station 244 is to read the bar code information on each test tube in order to access the customer's database from the control computer 202. This information will indicate the number of separations and the volume of each separation to be performed from the fluid sample in the test tube. From this information, the control computer 202 will calculate how much serum is needed to perform the aliquotting operation.

The bar code read station 244 preferably includes a bar code scanner which can make 400 scans per second. As the test tube enters the bar code read station 244, a gripper device grips the upper end of the test tube and lifts the test tube from conveyor fixture a slight distance. The test tube is then rotated approximately 360° such that the entire surface of the test tube will pass in front of the scanner. In this manner the scanner will have an opportunity to "read" the bar code label. The relative position of the bar code label to the scanner as the test tube enters the bar code read station 244 is therefore rendered irrelevant.

The bar code read station 244 will read the bar code label on the test tube, upload the information from the bar code label to the control computer 202, and then download the specimen aliquot requirements to the control system within the control computer 202.

Following the bar code read station 244, the test tubes are conveyed to the level sense station 250, which is designed to determine the level of serum in the test tube. The information extracted from the size sense station 240, the bar code read station 244, and the level sense station 250 verifies that there is a sufficient amount of liquid in the test tube to perform the required aliquotting operation.

In operation, a test tube is passed in front of the level sense station 250, and the level of serum is determined. By incorporating this calculation with the size of the test tube, determined from the size sense station 240, the quantity of liquid can then be ascertained and compared to the required amounts via the information supplied by the control computer 202. The test tube is then forwarded out of the sensing station 230, via the conveyor 212 to the next station in the automatic aliquotting system. At the test tube load station 260 if there is an insufficient amount of liquid in the test tube, the test tube is the removed from the conveyor 212 and placed in the reject bin 232 for manual processing.

Test Tube Load Station

After the test tubes have been judged to be an acceptable test tube via the operation of the sensing station 230, the accepted test tubes are forwarded by the conveyor 212 to a test tube load station 260, which is designed to load the test tubes from the conveyor 212 onto the index table 80 for dispensing and aliquotting the fluid sample. The test tube load station 260 includes a gripper apparatus 262 which grips the test tubes from the load station 260 and conveys them, via a slide track 264, to the index table 80.

Index Table

In this embodiment, the index table 80 is a generally horizontal rotating disc which passes the accepted test tubes to subsequent stations for processing. As illustrated in FIG. 11, the preferred embodiment of the index table 80 includes 4 stations of three test tube positioning slots 82, 84, 86.

In the first index table position, the loading area 266, the three test tube positioning slots 82, 84, 86 are positioned for receiving accepted test tubes from the test tube load station 260, via the gripper apparatus 262.

After the test tubes have been loaded onto the slots, 82, 84, 86, the index table 80 is rotated clock-wise to the sample fluid dispensing area 270. The sample fluid dispensing area 270 positions the test tubes for sample fluid withdrawal in substantially the same manner as that described previously with respect to FIGS. 3, 4, and 8. Reference is made to the previous discussion for an explanation of the sample collection station 100.

The third position, the test tube unload area 280 is designed to remove the completed test tubes from the apparatus in a manner to be described hereafter.

The fourth position 284 is an idle area wherein the slots 82, 84, 86 are empty.

Aliquot Station

After the fluid sample from the test tubes have been withdrawn according to the previously described manner, the sample fluid is ready to be aliquotted or dispensed into aliquot tubes in the aliquotting station 290.

Prior to the aliquotting operation, the aliquot tubes must be labeled. The aliquot labeling operation begins at the test tube sensing station 230. Once a test tube as been accepted for sample withdrawal, the appropriate number of aliquot tubes with related bar coded information must be automatically prepared and placed in the aliquot station 290 to receive the fluid sample. This is accomplished by a printer 292 which is electronically connected to the control computer 202. The control computer 202 sends a signal to the printer 292 to prepare a label for an aliquot tube which relates to an accepted fluid sample's aliquot. The unlabeled aliquot tubes are placed in a hopper 293 and positioned to receive a label from the printer 292 and then forwarded to the aliquot station 290 via a rotating star wheel 297 and a slide mechanism 299 to receive the fluid sample.

Figure 15:
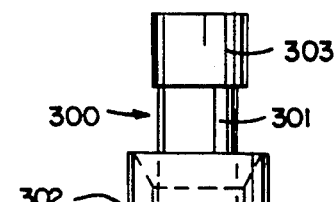
FIG. 15 is a partial side elevated view of the aliquot conveyor assembly of FIG. 14 taken along lines 15—15 of FIG. 14.
Figure 14:
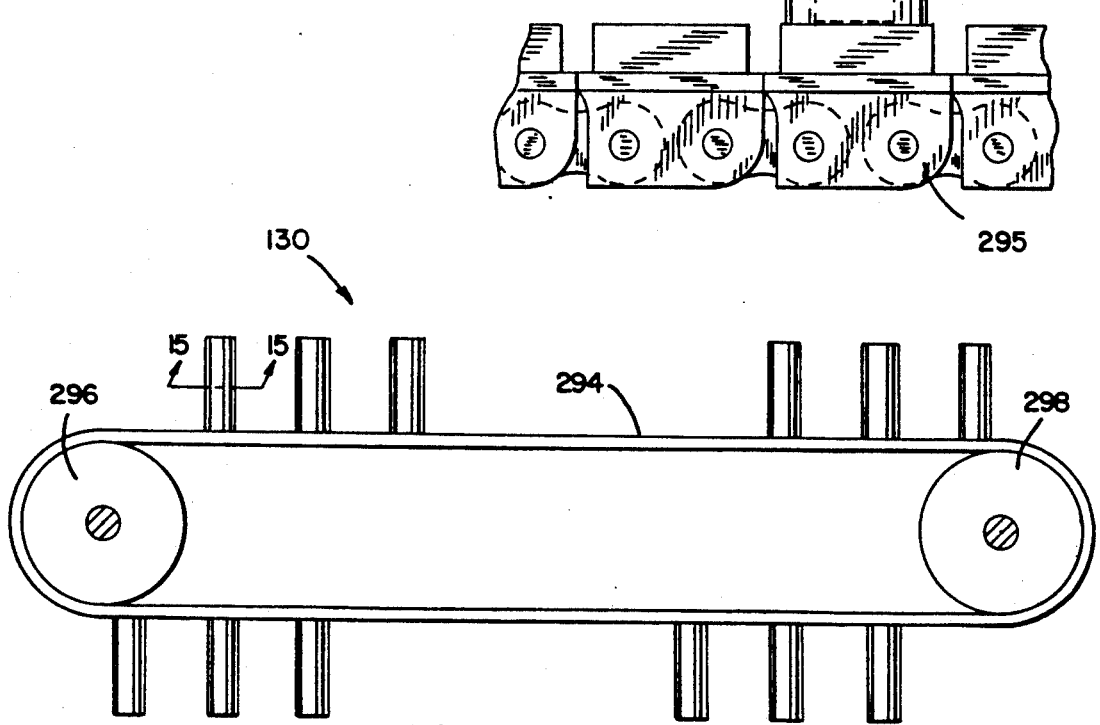
FIG. 14 is a side elevated view of the aliquot conveyor assembly of the sample fluid testing system illustrated in FIG. 11.

Reference is now made to FIGS. 14 and 15 for a description of the aliquot conveyor station 290 of this embodiment. The aliquot conveyor station 290 includes an endless conveyor belt 294 having a track system 295 designed to travel around rotating cylinders 296, 298 in a manner known to the art.

After the test tubes 10 have been loaded into the positioning slots 82, 84, 86 in the index table 80, labeled aliquot tubes 300 are loaded from the printer mechanism to the aliquot tube conveyor belt 294, which includes aliquot tube holders 302 suitable for holding the aliquot tubes 300.

The aliquot tubes 300 are standard aliquot tubes known to the art having a receptacle portion 301 and a cap 303. Without wishing to be limited to any one description, the aliquot receiving tubes 300 are preferably plastic 16 mm × 80 mm pre-capped vials. The cap 303 is preferably a self-sealing cap capable of receiving the needle 42 of the sample collection device 40. Like the test tube holders 222, the aliquot tube holders 302 are designed to receive the aliquot tubes 300 in a loose fitting manner.

The aliquot conveyor 294 moves a measured distance, as determined by the control computer 202, such that the correctly labeled aliquot tube 300 will be in position to receive its respective fluid sample from a test tube 10.

The index table 80 rotates clockwise to the sample fluid dispensing area 270 to present the test tubes directly over the sample collection devices 40, as illustrated in FIG. 8. The sample collection devices 40 elevate moving the needle 42 through the index table 80 and piercing the test tube 10. The fluid sample is then withdrawn from the test tubes 10 according to previously described conditions.

Once the fluid sample has been withdrawn, the sample collection devices 40 retract from the index table 80, as previously described, and the sample collection devices 40 rotate approximately 180° until the needles of the sample collection devices are pointing downwards.

The sample collection devices 40 then advance to the aliquot station 290 until they are directly over the rows of aliquot tubes 300 on the aliquot conveyor system 292.

The aliquot conveyor belt 294 is preferably arranged so that the aliquot tubes 300 are in three columns with five rows each. The columns are placed in alignment with each sample collection device. The five rows of aliquot tubes 300 will allow up to five aliquot tubes of dispensed fluid sample.

As the sample collection devices are placed over the first row of aliquot tubes, the activating cylinder 104 actuates lowering the sample collection devices 40 until the needles 42 pierce the cap 303 of the aliquot tube 300. A measured amount of fluid sample is then dispensed into each of the three aliquot tubes 300. Each sample collection device 40 is rigged to an independent pump. Thus, if only ½ ml is needed for the first column and 1 ml for the second column and 1½ ml for the third column, the system 200 can accommodate this arrangement.

Washing Station

After the appropriate volumes of serum have been dispensed from the collection devices 40, the now-used collection devices must be washed. The washing cycle is preferably accomplished according to the principles described with respect to the automatic sample collection system previously described.

One of the unique advantages of the present invention is accomplished in the wash station 150. In the prior art, the aliquotting station 290 had to be paused for a sufficient amount of time, i.e., approximately 30 seconds to one minute, in order to clean the sample collection devices 40 for reuse. This extended the time required for handling the serum operation. The present invention avoids this disadvantage by employing the tool change device 102, which allows the tooling bar 60 with sample collection devices 40 to be removed and passed onto the wash station 150, which will systematically wash the sample collection devices 40. At the same time, a different tooling bar 60 with a clean set of collection devices 40 may be "plugged" into the tool change device 102 to continue the serum collection and aliquotting operation.

Therefore, the wash station 150 can proceed at the same time serum is being collected thus saving serum collection time and also assuring adequate time to wash the collection devices.

Test Tube Unload Station

Once the sample fluid has been withdrawn from the test tubes, the index table 80 rotates another 90° to the test tube unload area 280. In this position, a master gripper arm 312 descends upon the completed test tubes, one at a time, to simultaneously release the gripper 88 and remove the test tubes from the index table 80.

When the master gripper arm 312 lifts the test tube 10 from the index table 80, the test tube is still in its inverted position. In order to store the complete test tubes cap-side up, the test tube is positioned in a reposition fixture 314 to allow the gripper arm 312 to reposition the grip placement on the test tube. The test tube 10 is then reverted to its normal upright position and moved to a receptacle 316 on a test tube unload index table 318. The receptacle 316 is generally a slotted box on the test tube unload index table 318. Assuming that the receptacle 316 is a 240-slot cardboard box, the system 200 is programmed to begin filling the receptacle 316 in the upper right hand corner, always moving across in a 45° position, in order to avoid interference with any previously placed test tubes.

At the same time that the test tube is placed in the box, its location in the box is recorded in the control computer 202, such that the exact patient number and location in the cardboard box is known.

When the box is filled, the index table 318 rotates a previously loaded empty box from position 320 into correct position for filling.

It is within the scope of the present invention to place sensors throughout the system to ensure that the apparatus is working correctly. For example, an optical sensor could be placed at the location of the empty box. If the box is missing the sensor's signals would warn the control computer 202 to shut down operations until the problem was rectified.

Thus, the fluid sample collection system of the present invention can be utilized in a number of ways. First, it can be effectively used to automatically withdraw serum from a test tube while avoiding the dangers of having the operator handle the serum or having the needle penetrate the separator gel. Further, the system of the present invention can effectively measure the level of the test tube and compare it to the required level, inputted in the control computer 202 of the present invention, to determine whether the test tube has a sufficient amount of liquid to be accepted for the serum withdrawal stage. Further still, the system of the present invention can advantageously aliquot defined quantities according to the parameters inputted in the control computer 202.

In the preferred mode of the automatic aliquotting system of the present invention, the system will accomplish an average of 1 complete aliquot/split every 10 seconds. Because each test tube may require from 2 to 5 splits, the average to be used for performance measurements shall be 2.5 splits per test tube, i.e., 6 test tubes per minute at 2.5 splits results in 15 aliquots per minute or 900 aliquots per hour.

It is understood that the invention is not confined to the particular construction and arrangement herein illustrated and described, but embraces such modified forms thereof as come within the scope of the following claims.

What is claimed is:

1. A fluid collection system for a plurality of test tubes, the system comprising means for selectively determining the quantity of fluid required to be withdrawn from an individual test tube, wherein the test tube has a closed end and an open end, the open end being sealed by a self-sealing cap, and a fluid collection device which comprises:

a. gripping means for releasibly holding the test tube in a substantially inverted vertical posture such that the sealed open end is situated at the bottom of the test tubes;

b. a fluid collection device positioned below the test tube, the fluid collection device including a penetrating and fluid-extracting needle having a distal and proximal end, wherein the distal end includes an orifice adapted to penetrate the self-sealing cap of the test tube such that the distal end of the needle barely penetrates the cap of the test tube, and a fluid collection container; and c. vacuum means connected to the fluid collection device and adapted to create a fluid withdrawing vacuum, a means to selectively control the vacuum means to withdraw a quantity of fluid previously determined to be required for the individual test tube.

2. The system according to claim 1 wherein the fluid collection container contains capillary tubing adapted to receive the fluid, the tubing having a first end and a second end, wherein the first end is connected to the needle and the second end is connected to the vacuum means.

3. The system according to claim 2 wherein the tubing has been previously filled with a pump fluid.

4. The system according to claim 2 wherein the vacuum means is a peristaltic pump.

* * * * *